United States Patent [19]

Arena

[11] Patent Number: 4,471,144

[45] Date of Patent: Sep. 11, 1984

[54] THETA-ALUMINA AS A HYDROTHERMALLY STABLE SUPPORT IN HYDROGENATION

[75] Inventor: Blaise J. Arena, Des Plaines, Ill.

[73] Assignee: UOP Inc., Des Plaines, Ill.

[21] Appl. No.: 449,044

[22] Filed: Dec. 13, 1982

[51] Int. Cl.$^3$ .................... C07C 29/136; C07C 29/14; C07C 31/26; C07C 31/18

[52] U.S. Cl. .................................... 568/863; 502/332

[58] Field of Search .......................................... 568/863

[56] References Cited

U.S. PATENT DOCUMENTS

| | | | |
|---|---|---|---|
| 2,868,847 | 1/1959 | Boyers ................................... | 568/863 |
| 4,221,738 | 9/1980 | Imai ............................... | 252/466 PT |
| 4,235,705 | 11/1980 | Antos ............................. | 252/466 PT |
| 4,264,475 | 4/1981 | Schoennagel ................ | 252/466 PT |
| 4,303,552 | 12/1981 | Ernest et al. .................. | 252/466 PT |
| 4,323,542 | 4/1982 | Joy ................................. | 252/466 PT |
| 4,338,221 | 7/1982 | Qualeatti ...................... | 252/466 PT |
| 4,380,680 | 4/1983 | Arena .................................... | 568/863 |

*Primary Examiner*—J. E. Evans
*Attorney, Agent, or Firm*—James R. Hoatson, Jr.; Eugene I. Snyder; William H. Page II

[57] ABSTRACT

Theta-alumina is a hydrothermally stable support which can be used advantageously as an inert carrier for metals effective as a hydrogenation catalyst, thereby affording means to conduct hydrogenation in aqueous media. Ruthenium on theta-alumina is especially effective in reducing aqueous solution of carbohydrates to their polyols with high conversion and, in the case of glucose, high selectivity to sorbitol.

10 Claims, No Drawings

THETA-ALUMINA AS A HYDROTHERMALLY STABLE SUPPORT IN HYDROGENATION

BACKGROUND OF THE INVENTION

In hydrogenating organic materials using zerovalent metal catalysts, it is more common to use the metal dispersed on an inert support than to use, for example, colloidal dispersions of the metal itself. Included among advantages accruing to supported metals are their greater surface area, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the lack of hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The irony in hydrogenating aqueous solutions of carbohydrates is two-fold. First, the reduction products of many carbohydrates are important materials of commerce; sorbitol and mannitol are but two common reduction products. Second, there is no practical alternative to using water as the solvent in hydrogenating carbohydrates because carbohydrates generally are insoluble or, at best, sparingly soluble in most organic solvents. Because carbohydrates are solids, it is operationally mandatory to use a solvent in their hydrogenation.

One aspect of this invention is a method of hydrogenating hydrogenatable organic material in aqueous solution using as a catalyst a metal on theta-alumina as a hydrothermally stable support. In another aspect this invention is a method of hydrogenating an aqueous solution of a carbohydrate where the catalyst is a Group VIII zerovalent metal dispersed on a support of theta-alumina. In one embodiment the metal is ruthenium. In a more specific embodiment the carbohydrate is a hexose.

DESCRIPTION OF THE INVENTION

One aspect of this invention is a method of hydrogenating a hydrogenatable organic material in aqueous solution comprising contacting the aqueous solution with hydrogen under hydrogenation conditions in the presence of a metal which is a hydrogenation catalyst dispersed on theta-alumina, and recovering the hydrogenated product.

Another aspect of the invention which is the subject matter herein is a method for the hydrogenation of a carbohydrate in aqueous solution to its polyols comprising contacting at hydrogenation conditions a reaction medium consisting essentially of said solution with hydrogen and a catalyst consisting essentially of ruthenium dispersed on theta-alumina, and recovering the formed polyols. This invention results from the discovery that theta-alumina possesses remarkable hydrothermal stability under conditions necessary for the hydrogenation of aqueous solutions of hydrogenatable organic materials, particularly carbohydrates, especially in comparison with the more commonly used gamma-alumina. Thus, whereas substantial amounts of silica and gamma-alumina, which are two commonly employed support materials, dissolve in the aqueous medium during hydrogenation of, for example, carbohydrates, virtually no leaching of theta-alumina occurs under comparable hydrogenation conditions.

Therefore, one advantage of this invention is that the product contains a substantially lower level of dissolved metal from the inert support described herein than that resulting from inert supports commonly employed previously in the hydrogenation of aqueous solutions of carbohydrates.

Another advantage of this invention is that the metals commonly employed as a hydrogenation catalyst retain their activity on the theta-alumina support of this invention.

Yet another advantage of the invention as claimed is that of the Group VIII metals ruthenium is more resistant to leaching under hydrogenation conditions than other Group VIII metals. Because ruthenium is both resistant to leaching and particularly catalytically active it is especially advantageous in the practice of this invention.

As mentioned previously, one aspect of the invention herein is a method of general utility for the hydrogenation of a hydrogenatable organic material in aqueous solution. The crux of this aspect of the invention is the use as a hydrogenation catalyst of a metal dispersed on theta-alumina. The metals used are those known to be effective in catalyzing hydrogenation. It is to be emphasized that the essence of this aspect of the invention is the use of theta-alumina as a hydrothermally stable support for metals catalytically active in hydrogenation, thereby conferring advantages on a method utilizing such a metal-support combination for hydrogenation in an aqueous medium. Among the metals which may be used are vanadium, chromium, manganese, iron, cobalt, nickel, copper, molybdenum, technetium, ruthenium, rhodium, palladium, silver, tungsten, rhenium, osmium, iridium, and platinum. Generally such metals will be in their zerovalent state, but some metallic compounds, such as copper chromite, are catalytically active per se, not being reduced to their zerovalent state even in situ.

The hydrogenation conditions include such variables as temperature, hydrogen pressure, and catalyst concentration, which will depend on the particular metal used and specific organic material to be hydrogenated, inter alia. For example, where simple unhindered alkenes, such as 3-hexene, are hydrogenated using palladium, a catalyst concentration from about 0.001 to about 0.5% metal, a temperature from about 50° C. to about 200° C., and a hydrogen pressure from one atmosphere up to several atmospheres will suffice. Using an aromatic compound as a substrate, for example benzene, and the same metal and concentration as before, a somewhat higher temperature from about 125° C. to about 250° C. at a pressure from several to several hundred atmospheres are appropriate. Although it is not feasible to list all appropriate hydrogenation conditions these are readily determined by one skilled in the art in the practice of this invention.

Another aspect of the invention herein is concerned with a method of hydrogenating a carbohydrate to its polyols. Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, the polyol is a tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abundant polysaccharides which may be employed in this invention are starch, cellulose and their degradation products.

The catalyst of this aspect of the invention consists essentially of zerovalent ruthenium dispersed on theta-alumina. Such a catalyst is prepared by impregnating theta-alumina with a suitable ruthenium salt, optionally calcining the salt, and reducing it to the zerovalent metal in a hydrogen atmosphere. It has been found that although calcination in an inert atmosphere at a temperature from about 200° C. to about 500° C. affords a satisfactory catalyst, it is preferable to omit the calcination and reduce the ruthenium salt in flowing hydrogen at a temperature between about 140° C. and about 500° C., but preferably between about 300° C. and about 500° C.

It is to be understood that by theta-alumina is meant alumina whose crystallinity as measured by X-ray diffraction corresponds to that characterized in the Joint Committee on Powder Diffraction Standards number 23-1009. Because the surface area of theta-alumina is low relative to, e.g., gamma-alumina, metal loadings are correspondingly low. In this invention the catalyst typically contains from about 1 to about 10% metal.

The aqueous solution of the carbohydrate is contacted with hydrogen and the catalyst of this invention at hydrogenation conditions. Hydrogenation conditions include a pressure of at least about 200 psig, with pressures in excess of about 5000 psig generally not advantageous. In the usual case, a hydrogen pressure from about 700 to about 5000 psig is used, with a pressure from about 1000 to about 3000 psig preferred. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred with one from about 105° to about 130° C. being especially advantageous.

The amount of catalyst used will depend, inter alia, on the amount of metal on the support, hydrogenation pressure, and temperature. Usually, sufficient catalyst is employed to give from about 0.1 to about 1 wt. % ruthenium based on the carbohydrate as monosaccharide.

The method of this invention may be practiced in either a batch or a fixed mode. In the batch mode, an aqueous solution of the carbohydrate containing from about 25 to about 60 percent carbohydrates is loaded into a reactor containing the ruthenium on theta-alumina catalyst of this invention in an amount sufficient to give from about 0.1 to about 1 wt. % ruthenium based on the carbohydrate. The mixture is then heated to the desired temperature, which is from about 80° to about 160° C., and usually from about 100° to about 150° C. After the desired reaction temperature is attained, hydrogen is admitted to a pressure from about 700 to about 5000 psig. The entire reaction mixture is then agitated to provide adequate contact among the hydrogen, catalyst, and carbohydrate. The hydrogenation is continued until there is no further hydrogen uptake, which generally is a time from about 0.5 to about 5 hours.

The invention described is advantageously practiced in a continuous fashion using the catalyst in a fixed bed, fluidized bed, expanded bed, and so forth. In a typical operation, feedstock containing from about 25 to about 60% of the carbohydrate(s) to be reduced is passed through the bed of ruthenium on theta-alumina in a hydrogen atmosphere. Hydrogen pressure is from about 700 to about 5000 psig, and bed temperature is generally from about 100 to about 150° C. The effluent is an aqueous solution of the formed polyol(s), which may be recovered, for example, by removal of water by evaporation.

The examples which follow merely illustrate this invention and are not intended to limit it in any way.

Continuous reductions were performed in a ⅞" I.D. vertical tube reactor with a spiral preheater and with a bed of 100 cc (135 g) catalyst prepared in accord with the general directions of Example 1. The feedstock, passed downflow, was an oxygen-free 50% aqueous solution of glucose at pH about 5.5. Hydrogen was introduced at a 10:1 molar ratio relative to glucose. Effluent was analyzed by high pressure liquid chromatography for sorbitol, mannitol, fructose, and glucose.

EXAMPLE 1

The following description is representative of the preparation of the catalysts of this invention, with the variables being limited to the presence or absence of calcination in nitrogen and the reduction temperature. A solution of 11 g $RuCl_3 \cdot 3H_2O$ in 280 ml deionized water was mixed with 138 g theta-alumina and water was evaporated with gentle heating. The impregnated alumina was placed in a vertical tube furnace and calcined, if at all, in flowing nitrogen for 3 hours at 410° C., then reduced in flowing hydrogen for 3 hours at 410° C.

EXAMPLE 2

The effect of various process variables (temperature, pressure, and liquid hourly space velocity) on conversion of glucose and selectivity of sorbitol formation were scanned using a 3% ruthenium on theta-alumina calcined, then reduced, at 410° C. Table 1 displays some reprentative results. Effluent also was analyzed periodically both for leaching of aluminum and ruthenium, with results being presented in Table 2.

TABLE 1

Continuous Reduction of Glucose, 3% Ru on Theta-Alumina, Calcined in $N_2$ @ 410°C., Reduced in $H_2$ @ 410° C.

| $P^a$ | $T^b$ | $LHSV^c$ | Conversion$^d$ | Selectivity$^e$ |
|---|---|---|---|---|
| 700 | 120 | 1.0 | 97 | 96 |
| 700 | 120 | 0.5 | 98 | 94 |
| 700 | 120 | 2.0 | 63 | 96 |
| 2000 | 120 | 2.5 | 76 | 97 |
| 2000 | 120 | 1.0 | 99 | 97 |
| 2000 | 120 | 0.5 | 99 | 96 |
| 1500 | 120 | 1.0 | 99 | |
| 2000 | 120 | 1.5 | 93 | 97 |
| 700 | 120 | 1.0 | 86 | 96 |
| 700 | 130 | 1.0 | 94 | 94 |
| 700 | 110 | 1.0 | 72 | 97 |

$^a$Hydrogen pressure, psig
$^b$Temperature, °C.
$^c$Liquid hourly space velocity
$^d$Percent glucose reacted
$^e$Percentage of sorbitol in total product mix. Other products include mannitol, fructose, and iditol.

TABLE 2

Leaching in Continuous Reduction

| Time on Stream (hrs) | Al, ppm | Ru, ppm |
|---|---|---|
| 12 | 9.4 | <1 |
| 32 | 4.8 | |
| 84 | 0.4 | <1 |
| 180 | 0.2 | <1 |
| 252 | 0.3 | <1 |

EXAMPLE 3

Three catalysts of 3% ruthenium on theta-alumina were prepared using reduction temperature and calcination as variables. Catalyst A was calcined in nitrogen at 410° C., then reduced at 410° C. Catalyst B was not calcined and was reduced at 410° C. Catalyst C also was not calcined but was reduced at 145° C. Continuous reductions were performed over a fixed bed of each catalyst at 2300 psig hydrogen at 1.0 LHSV for at least 200 hours, with the range of observed results presented in Table 3.

TABLE 3

Effect of Catalyst Preparation of Continuous Reduction of Glucose

| Catalyst | T, °C. | Conversion | Selectivity |
|---|---|---|---|
| A | 120 | 99.4–99.9 | 92.2–94.0 |
| B | 106 | 99.8–99.9 | 91.6–94.0 |
| C | 110 | 99.8–99.9 | 85.7–88.4 |

Comparison of entries for A and B shows that omitting calcination affords a more active catalyst, as indicated by the lower operating temperature. The conversion with catalyst A declined over a 200 hour test run whereas that with catalyst B remained steady, showing that the absence of calcination affords a more stable catalyst, i.e., one with a longer effective lifetime. Catalyst C shows that lowering the reduction temperature adversely affects the selectivity characteristics of the resulting catalyst.

What is claimed is:

1. A method of hydrogenating a carbohydrate in aqueous solution to its polyols comprising contacting at hydrogenation conditions a reaction medium consisting essentially of said solution with hydrogen and a catalyst consisting essentially of zerovalent ruthenium dispersed on theta-alumina, and recovering the formed polyols.

2. The method of claim 1 where the carbohydrate is a monosaccharide.

3. The method of claim 2 where the monosaccharide is selected from the group consisting of hexoses, pentoses, and tetroses.

4. The method of claim 3 where the monosaccharide is a hexose and the polyol is a hexitol.

5. The method of claim 4 where the hexose is glucose or mannose and the hexitol is sorbitol or mannitol, respectively.

6. The method of claim 4 wherein the hexose is fructose and the polyol is a mixture of sorbitol and mannitol.

7. The method of claim 1 where the hydrogenation conditions include a hydrogen pressure from about 700 to about 5000 psig and a temperature from about 80° to about 160° C.

8. The method of claim 7 where the pressure is from about 1000 to about 3000 psig.

9. The method of claim 7 where the temperature is from about 100° to about 150° C.

10. The method of claim 9 where the temperature is from about 105° to about 130° C.

* * * * *